United States Patent
Benner et al.

(10) Patent No.: US 7,026,270 B2
(45) Date of Patent: Apr. 11, 2006

(54) BIOCIDAL COMPOUNDS AND THEIR PREPARATION

(75) Inventors: Jill Patricia Benner, Bracknell (GB); Bettina Gertrud Henriette Boehlendorf, Basel (CH); Martin Richard Kipps, Berkshire (GB); Nicolas Eugene Paul Lambert, Basel (CH); Riet Luck, Basel (CH); Louis-Pierre Molleyres, Basel (CH); Snezana Neff, Basel (CH); Traugott Christoph Schuez, Basel (CH); Paul David Stanley, Bracknell (GB)

(73) Assignee: Syngenta Crop Protection, Inc., Greensboro, NC (US)

( * ) Notice: Subject to any disclaimer, the term of this patent is extended or adjusted under 35 U.S.C. 154(b) by 0 days.

(21) Appl. No.: 10/501,816

(22) PCT Filed: Jan. 10, 2003

(86) PCT No.: PCT/GB03/00063

§ 371 (c)(1),
(2), (4) Date: Nov. 22, 2004

(87) PCT Pub. No.: WO03/062242

PCT Pub. Date: Jul. 31, 2003

(65) Prior Publication Data

US 2005/0096229 A1    May 5, 2005

(30) Foreign Application Priority Data

Jan. 18, 2002  (GB) ................................. 0201160

(51) Int. Cl.
*A01N 25/00* (2006.01)
*A01N 43/00* (2006.01)
*A01N 43/60* (2006.01)
*A01N 239/02* (2006.01)
*A01N 401/00* (2006.01)

(52) U.S. Cl. .............. 504/116.1; 504/129; 504/130; 504/136; 544/298; 544/309; 544/310; 544/311; 514/247; 514/252.01; 424/405

(58) Field of Classification Search ............ 544/242, 544/245, 249, 298, 309, 310, 311; 504/129, 504/130, 136; 424/404; 514/247, 252.1
See application file for complete search history.

(56) References Cited

U.S. PATENT DOCUMENTS 6,147,230 A    11/2000  Shimamoto et al. ........ 549/396

OTHER PUBLICATIONS

DN 84:4395, HCAPLUS, abstract of Sakata, Kanzo et al., Tetrahederon Latters, (1975), (37), 3191, 3191-94.*
DN 90:23481, HCAPLUS, abstract of Sakato, Kanzo et al., Organic Magnetic Resonance (1977), 10, 230-4.*
DN 87:23659, HCAPLUS, abstract of Sakato, Kanzo, Agricultural and Biological Chemistry (1977), 41(2), 413-415.*
Hanessian et al., AN2003:805261 HCAPLUS, abstract of Organic Letters (2003), 5(23), 4277-4280.*
Spencer Knapp et al: "Synthesis of Ezomycin Octosyl Nucleoside"; Journal of Organic Chemistry, vol. 59, No. 5, 1994, pp. 946-948.

* cited by examiner

Primary Examiner—Sabiha Qazi
(74) Attorney, Agent, or Firm—Thomas Hamilton

(57) ABSTRACT

This invention concerns new biocidal compounds of formula (I) wherein R is H or $CH_3$. Of particular interest are two isomers that are named malayamycin A and desmethylmalayamycin A. These isomers, which may be prepared by growing under controlled conditions a previously unknown strain of micro-organism from the species *Streptomyces malaysiensis*, are characterised by nmr and mass spectroscopic data. They have biocidal activity, including anti-fungal, anti-viral and anti-cancer activity, and are of special interest for use in agriculture, horticulture, animal and human health.

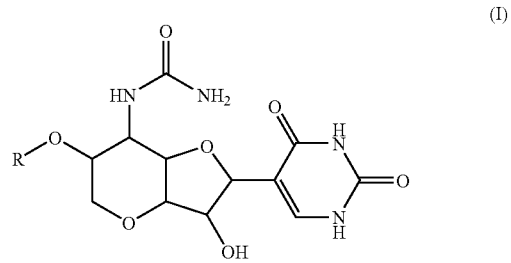

(I)

9 Claims, No Drawings

BIOCIDAL COMPOUNDS AND THEIR PREPARATION

This application is a 371 of International Application No. PCT/GB03/00063 filed Jan. 10, 2003, which claims priority to GB 0201160.9, filed Jan. 18, 2002, the contents of which are incorporated herein by reference.

This invention relates to new biocidal compounds and to a process for their preparation. More particularly it relates to biocidal compounds which may be obtained by cultivation of *Streptomyces* organisms; to the use of said compounds as biocides; to compositions containing a biocidally effective amount of said compounds; a method of combating pathogens using said compounds; a new strain of *Streptomyces malaysiensis* and mutants thereof.

In a first aspect the invention provides a new biocidal compound of formula (I)

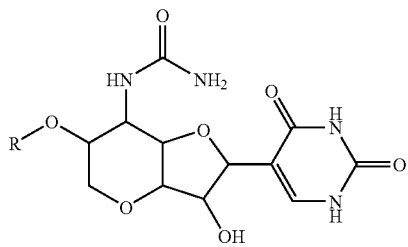

wherein R is H or $CH_3$.

The compound where R is H and the compound where R is $CH_3$ are novel compounds not previously isolated. They are characterised by the nmr and mass spectroscopy data provided in the examples herein. They may be prepared by growing under controlled conditions, a previously unknown strain of micro-organism from the species *Streptomyces malaysiensis*. The compounds of the invention have biocidal activity and, in particular, anti-fungal, anti-viral and anti-cancer activity and are of special interest for use in agriculture, horticulture, animal and human health. The compounds may also be of use as intermediates in the preparation of further active compounds. The compounds of formula (I) may be obtained by fermentation and recovered in substantially pure form as described herein.

The compounds of formula (I) have six asymmetric centres and may exist in the form of one or more isomers. The invention includes all isomers, individually or in a mixture of one or more forms. The compounds of the invention may exist in several tautomeric forms and the invention extends to all forms.

Of particular interest are the compounds of formulae (II) and (III), which are here named malayamycin A and desmethylmalayamycin A, respectively.

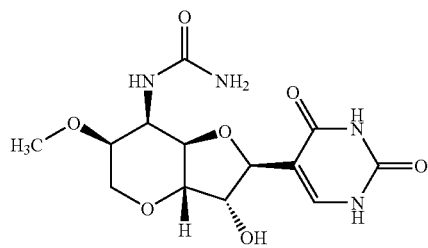

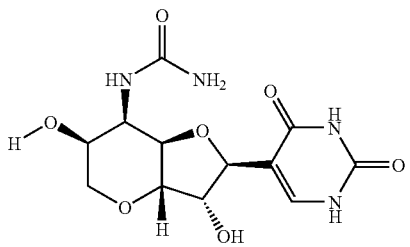

The compounds of formulae (II) and (III) may exist in alternative tautomeric forms and the invention extends to said alternative forms.

The compounds of formula (I) are biocidal agents. They are active antiviral agents showing for example antiviral activity against the Human Immunodeficiency Virus associated with the disease AIDS. They have also been shown to have anti-cancer properties. For example they show an in inhibitory effect on the cell proliferation of cancer cells. As used herein the term biocidal is used to cover activity against pathogens and includes antiviral, antifungal and anticancer activity. The use of the compounds as antifungal agents, particularly against plant pathogenic fungi, is of particular interest.

The compounds of formula (I) are active fungicides and may be used to control one or more of the following plant pathogens: *Pyricularia oryzae* (*Magnaporthe grisea*) on rice and wheat and other *Pyricularia* spp. on other hosts; *Puccinia triticina* (or *recondita*), *Puccinia striiformis* and other rusts on wheat, *Puccinia hordei, Puccinia striiformis* and other rusts on barley, and rusts on other hosts (for example turf, rye, coffee, pears, apples, peanuts, sugar beet, vegetables and ornamental plants); *Erysiphe cichoracearum* on cucurbits (for example melon); *Blumeria* (or *Erysiphe*) *graminis* (powdery mildew) on barley, wheat, rye and turf and other powdery mildews on various hosts, such as *Sphaerotheca macularis* on hops, *Sphaerothecafusca* (*Sphaerotheca fultiginea*) on cucurbits (for example cucumber), *Leveillula taurica* on tomatoes, aubergine and green pepper, *Podosphaera leucotricha* on apples and *Uncinula necator* on vines; *Cochliobolus* spp., *Helminthosporium* spp., *Drechslera* spp. (*Pyrenophora* spp.), *Rhynchosporium* spp., *Mycosphaerella graminicola* (*Septoria tritici*) and *Phaeosphaeria nodoruin* (*Stagonospora nodorum* or *Septoria nodorum*), *Pseudocercosporella herpotrichoides* and *Gaeumannomyces graminis* on cereals (for example wheat, barley, rye), turf and other hosts; *Cercospora arachidicola* and *Cercosporidium personatum* on peanuts and other *Cercospora* spp. on other hosts, for example sugar beet, bananas, soya beans and rice; *Botrytis cinerea* (grey mould) on tomatoes, strawberries, vegetables, vines and other hosts and other *Botrytis* spp. on other hosts; *Alternaria* spp. on vegetables (for example carrots), oil-seed rape, apples, tomatoes, potatoes, cereals (for example wheat) and other hosts; *Venturia* spp. (including *Venturia inaequalis* (scab)) on apples, pears, stone fruit, tree nuts and other hosts; *Cladosporium* spp. on a range of hosts including cereals (for example wheat) and tomatoes; *Monilinia* spp. on stone fruit, tree nuts and other hosts; *Didymella* spp. on tomatoes, turf, wheat, cucurbits and other hosts; *Phoma* spp. on oil-seed rape, turf, rice, potatoes, wheat and other hosts; *Aspergillus* spp. and *Aureobasidium* spp. on wheat, lumber and other hosts; *Ascochyta* spp. on peas, wheat, barley and other hosts; *Stemphylium* spp. (*Pleospora* spp.) on apples, pears, onions and other hosts; summer diseases (for example bitter rot (*Glomerella cingulata*), black rot or frogeye leaf spot (*Bot-* ryosphaeria obtusa), Brooks fruit spot (*Mycosphaerella pomi*), Cedar apple rust (*Gymnosporangium juniperi-virginianae*), sooty blotch (*Gloeodes pomigena*), flyspeck (*Schizothyrium pomi*) and white rot (*Botryosphaeria dothidea*)) on apples and pears; *Plasmopara viticola* on vines; other downy mildews, such as *Bremia lactucae* on lettuce, *Peronospora* spp. on soybeans, tobacco, onions and other hosts, *Pseudoperonospora humuli* on hops and *Pseudoperonospora cubensis* on cucurbits; *Pythium* spp. (including *Pythium ultimum*) on turf and other hosts; *Phytophthora infestans* on potatoes and tomatoes and other *Phytophthora* spp. on vegetables, strawberries, avocado, pepper, ornamentals, tobacco, cocoa and other hosts; *Thanatephorus cucumeris* on rice and turf and other *Rhizoctonia* spp. on various hosts such as wheat and barley, peanuts, vegetables, cotton and turf; *Sclerotinia* spp. on turf, peanuts, potatoes, oil-seed rape and other hosts; *Sclerotium* spp. on turf, peanuts and other hosts; *Gibberella fujikuroi* on rice; *Colletotrichum* spp. on a range of hosts including turf, coffee and vegetables; *Laetisaria fuciformis* on turf; *Mycosphaerella* spp. on bananas, peanuts, citrus, pecans, papaya and other hosts; *Diaporthe* spp. on citrus, soybean, melon, pears, lupin and other hosts; *Elsinoe* spp. on citrus, vines, olives, pecans, roses and other hosts; *Verticillium* spp. on a range of hosts including hops, potatoes and tomatoes; *Pyrenopeziza* spp. on oil-seed rape and other hosts; *Oncobasidium theobromae* on cocoa causing vascular streak dieback; *Fusarium* spp., *Typhula* spp., *Microdochium nivale, Ustilago* spp., *Urocystis* spp., *Tilletia* spp. and *Claviceps purpurea* on a variety of hosts but particularly wheat, barley, turf and maize; *Ramularia* spp. on sugar beet, barley and other hosts; post-harvest diseases particularly of fruit (for example *Penicillium digitatum, Penicillium italicum* and *Trichoderma viride* on oranges, *Colletotrichum musae* and *Gloeosporium inusarum* on bananas and *Botrytis cinerea* on grapes); other pathogens on vines, notably *Eutypa lata, Guignardia bidwellii, Phellinus igniarus, Phomopsis viticola, Pseudopeziza tracheiphila* and *Stereum hirsutum*; other pathogens on trees (for example *Lophodernium seditiosum*) or lumber, notably *Cephaloascusfragrans, Ceratocystis* spp., *Ophiostoma piceae, Penicillium* spp., *Trichoderma pseudokoningii, Trichoderma viride, Trichodenna harzianum, Aspergillus niger, Leptographium lindbergi* and *Aureobasidium pullulans*; and fungal vectors of viral diseases (for example *Polymyxa graminis* on cereals as the vector of barley yellow mosaic virus (BYMV) and *Polymyxa betae* on sugar beet as the vector of rhizomania).

The compounds of formula (I) may move acropetally, basipetally or locally in plant tissue to be active against one or more fungi.

The invention therefore provides a method of combating or controlling phytopathogenic fungi which comprises applying a fungicidally effective amount of a compound of formula (I), or a composition containing a compound of formula (I), to a plant, to a seed of a plant, to the locus of the plant or seed or to soil or any other plant growth medium, e.g. nutrient solution.

The term "plant" as used herein includes seedlings, bushes and trees. Furthermore, the fungicidal method of the invention includes protectant, curative, systemic, eradicant and antisporulant treatments.

The compounds of formula (I) are preferably used for agricultural, horticultural and turfgrass purposes in the form of a composition.

In order to apply a compound of formula (I) to a plant, to a seed of a plant, to the locus of the plant or seed or to soil or any other growth medium, a compound of formula (I) is usually formulated into a composition which includes, in addition to the compound of formula (I), a suitable inert diluent or carrier and, optionally, a surface active agent (SFA). SFAs are chemicals which are able to modify the properties of an interface (for example, liquid/solid, liquid/air or liquid/liquid interfaces) by lowering the interfacial tension and thereby leading to changes in other properties (for example dispersion, emulsification and wetting). It is preferred that all compositions (both solid and liquid formulations) comprise, by weight, 0.0001 to 95%, more preferably 1 to 85%, for example 5 to 60%, of a compound of formula (I). The composition is generally used for the control of fungi such that a compound of formula (I) is applied at a rate of from 0.1 g to 10 kg per hectare, preferably from 1 g to 6 kg per hectare, more preferably from 1 g to 1 kg per hectare.

When used in a seed dressing, a compound of formula (I) is used at a rate of 0.0001 g to 10 g (for example 0.001 g or 0.05 g), preferably 0.005 g to 10 g, more preferably 0.005 g to 4 g, per kilogram of seed.

In another aspect the present invention provides a biocidal composition comprising a biocidally effective amount of a compound of formula (I) and a suitable carrier or diluent therefor.

In a preferred embodiment of this aspect the present invention provides an antiviral composition comprising an antivirally effective amount of a compound of formula (I) and a suitable carrier or diluent therefor.

In a further preferred embodiment of this aspect the present invention provides an anti-cancer composition comprising an effective amount of a compound of formula (I) which is effective in reducing the proliferation of cancer cells and a suitable carrier or diluent therefor.

In a particularly preferred embodiment of this aspect the present invention provides a fungicidal composition comprising a fungicidally effective amount of a compound of formula (I) and a suitable carrier or diluent therefor.

In a still further aspect the invention provides a method of combating and controlling viruses which comprises treating the viruses or the locus of the viruses with an antivirally effective amount of a composition comprising a compound of formula (I).

In a still further aspect the invention provides a method of combating and controlling cancer cells which comprises treating the cancer cells or the locus of the cancer cells with an effective amount of a composition comprising a compound of formula (I) said amount being effective in reducing the proliferation of said cancer cells.

In a still further preferred aspect the invention provides a method of combating and controlling fungi which comprises treating the fungi or the locus of the fungi with a fungicidally effective amount of a composition comprising a compound of formula (I).

The compositions can be chosen from a number of formulation types, including dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), microemulsions (ME), suspension concentrates (SC), aerosols, fogging/smoke formulations, capsule suspensions (CS) and seed treatment formulations. The formulation type chosen in any instance will depend upon the particular purpose envisaged and the physical, chemical and biological properties of the compound of formula (I).

Dustable powders (DP) may be prepared by mixing a compound of formula (I) with one or more solid diluents (for example natural clays, kaolin, pyrophyllite, bentonite, alumina, montmorillonite, kieselguhr, chalk, diatomaceous earths, calcium phosphates, calcium and magnesium carbonates, sulphur, lime, flours, talc and other organic and inorganic solid carriers) and mechanically grinding the mixture to a fine powder.

Soluble powders (SP) may be prepared by mixing a compound of formula (I) with one or more water-soluble inorganic salts (such as sodium bicarbonate, sodium carbonate or magnesium sulphate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of formula (I) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of formula (I) and one or more powdered solid diluents or carriers, or from pre-formed blank granules by absorbing a compound of formula (I) (or a solution thereof, in a suitable agent) in a porous granular material (such as pumice, attapulgite clays, fuller's earth, kieselguhr, diatomaceous earths or ground corn cobs) or by adsorbing a compound of formula (I) (or a solution thereof, in a suitable agent) on to a hard core material (such as sands, silicates, mineral carbonates, sulphates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of formula (I) in water or an organic solvent, such as a ketone, alcohol or glycol ether. These solutions may contain a surface active agent (for example to improve water dilution or prevent crystallisation in a spray tank).

Emulsifiable concentrates (EC) or oil-in-water emulsions (EW) may be prepared by dissolving a compound of formula (I) in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclo-hexanone) and alcohols (such as benzyl alcohol, furfuryl alcohol or butanol), N-alkylpyrroli-dones (such as N-methylpyrrolidone or N-octylpyrrolidone), dimethyl amides of fatty acids (such as $C_8$–$C_{10}$ fatty acid dimethylamide) and chlorinated hydrocarbons. An EC product may spontaneously emulsify on addition to water, to produce an emulsion with sufficient stability to allow spray application through appropriate equipment. Preparation of an EW involves obtaining a compound of formula (I) either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of formula (I) is present initially in either the water or the solvent/SFA blend. Suitable solvents for use in MEs include those hereinbefore described for use in in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of formula (I). SCs may be prepared by ball or bead milling the solid compound of formula (I) in a suitable medium, optionally with one or more dispersing agents, to produce a fine particle suspension of the compound. One or more wetting agents may be included in the composition and a suspending agent may be included to reduce the rate at which the particles settle. Alternatively, a compound of formula (I) may be dry milled and added to water, containing agents hereinbefore described, to produce the desired end product.

Aerosol formulations comprise a compound of formula (I) and a suitable propellant (for example n-butane). A compound of formula (I) may also be dissolved or dispersed in a suitable medium (for example water or a water miscible liquid, such as n-propanol) to provide compositions for use in non-pressurised, hand-actuated spray pumps.

A compound of formula (I) may be mixed in the dry state with a pyrotechnic mixture to form a composition suitable for generating, in an enclosed space, a smoke containing the compound.

Capsule suspensions (CS) may be prepared in a manner similar to the preparation of EW formulations but with an additional polymerisation stage such that an aqueous dispersion of oil droplets is obtained, in which each oil droplet is encapsulated by a polymeric shell and contains a compound of formula (I) and, optionally, a carrier or diluent therefor. The polymeric shell may be produced by either an interfacial polycondensation reaction or by a coacervation procedure. The compositions may provide for controlled release of the compound of formula (I) and they may be used for seed treatment. A compound of formula (I) may also be formulated in a biodegradable polymeric matrix to provide a slow, controlled release of the compound.

A composition may include one or more additives to improve the biological performance of the composition (for example by improving wetting, retention or distribution on surfaces; resistance to rain on treated surfaces; or uptake or mobility of a compound of formula (I)). Such additives include surface-active agents, spray additives based on oils, for example certain mineral oils or natural plant oils (such as soy bean and rape seed oil), and blends of these with other bio-enhancing adjuvants (ingredients which may aid or modify the action of a compound of formula (I)).

A compound of formula (I) may also be formulated for use as a seed treatment, for example as a powder composition, including a powder for dry seed treatment (DS), a water soluble powder (SS) or a water dispersible powder for slurry treatment (WS), or as a liquid composition, including a flowable concentrate (FS), a solution (LS) or a capsule suspension (CS). The preparations of DS, SS, WS, FS and LS compositions are very similar to those of, respectively, DP, SP, WP, SC and DC compositions described above. Compositions for treating seed may include an agent for assisting the adhesion of the composition to the seed (for example a mineral oil or a film-forming barrier).

Wetting agents, dispersing agents and emulsifying agents may be SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulphuric acid (for example sodium lauryl sulphate), salts of sulphonated aromatic compounds (for example sodium dodecylbenzenesulphonate, calcium dodecyl-benzenesulphonate, butylnaphthalene sulphonate and mixtures of sodium di-isopropyl- and tri-isopropyl-naphthalene sulphonates), ether sulphates, alcohol ether sulphates (for example sodium laureth-3-sulphate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulphosuccinamates, paraffin or olefine sulphonates, taurates and lignosulphonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

A compound of formula (I) may be applied by any of the known means of applying fungicidal compounds. For example, it may be applied, formulated or unformulated, to any part of the plant, including the foliage, stems, branches or roots, to the seed before it is planted or to other media in which plants are growing or are to be planted (such as soil surrounding the roots, the soil generally, paddy water or hydroponic culture systems), directly or it may be sprayed on, dusted on, applied by dipping, applied as a cream or paste formulation, applied as a vapour or applied through distribution or incorporation of a composition (such as a granular composition or a composition packed in a water-soluble bag) in soil or an aqueous environment.

A compound of formula (I) may also be injected into plants or sprayed onto vegetation using electrodynamic spraying techniques or other low volume methods, or applied by land or aerial irrigation systems.

Compositions for use as aqueous preparations (aqueous solutions or dispersions) are generally supplied in the form of a concentrate containing a high proportion of the active ingredient, the concentrate being added to water before use. These concentrates, which may include DCs, SCs, ECs, EWs, MEs SGs, SPs, WPs, WGs and CSs, are often required to withstand storage for prolonged periods and, after such storage, to be capable of addition to water to form aqueous preparations which remain homogeneous for a sufficient time to enable them to be applied by conventional spray equipment. Such aqueous preparations may contain varying amounts of a compound of formula (I) (for example 0.0001 to 10%, by weight) depending upon the purpose for which they are to be used.

A compound of formula (I) may be used in mixtures with fertilisers (for example nitrogen-, potassium- or phosphorus-containing fertilisers). Suitable formulation types include granules of fertiliser. The mixtures suitably contain up to 25% by weight of the compound of formula (I).

The invention therefore also provides a fertiliser composition comprising a fertiliser and a compound of formula (I).

The compositions of this invention may contain other compounds having biological activity, for example micronutrients or compounds having similar or complementary fungicidal activity or which possess plant growth regulating, herbicidal, insecticidal, nematicidal or acaricidal activity.

By including another fungicide, the resulting composition may have a broader spectrum of activity or a greater level of intrinsic activity than the compound of formula (I) alone. Further the other fungicide may have a synergistic effect on the fungicidal activity of the compound of formula (I).

The compound of formula (I) may be the sole active ingredient of the composition or it may be admixed with one or more additional active ingredients such as a pesticide, fungicide, synergist, herbicide or plant growth regulator where appropriate. An additional active ingredient may: provide a composition having a broader spectrum of activity or increased persistence at a locus; synergise the activity or complement the activity (for example by increasing the speed of effect or overcoming repellency) of the compound of formula (I); or help to overcome or prevent the development of resistance to individual components. The particular additional active ingredient will depend upon the intended utility of the composition.

Examples of fungicidal compounds which may be included in the composition of the invention are AC 382042 (N-(1-cyano-1,2-dimethylpropyl)-2-(2,4-dichlorophenoxy) pro-pionamide), acibenzolar-S-methyl, alanycarb, aldimorph, anilazine, azaconazole, azafenidin, azoxystrobin, benalaxyl, benomyl, benthiavalicarb, biloxazol, bitertanol, blasticidin S, boscalid (new name for nicobifen), bromuconazole, bupirimate, captafol, captan, carbendazim, carbendazim chlorhydrate, carboxin, carpropamid, carvone, CGA 41396, CGA 41397, chinomethionate, chlorbenzthiazone, chlorothalonil, chlorozolinate, clozylacon, copper containing compounds such as copper oxychloride, copper oxyquinolate, copper sulphate, copper tallate, and Bordeaux mixture, cyamidazosulfamid, cyazofamid (IKF-916), cyflufenamid, cymoxanil, cyproconazole, cyprodinil, debacarb, di-2-pyridyl disulphide 1,1'-dioxide, dichlofluanid, diclocymet, diclomezine, dicloran, diethofencarb, difenoconazole, difenzoquat, diflumetorim, O,O-di-iso-propyl-S-benzyl thiophosphate, dimefluazole, dimetconazole, dimethirimol, dimethomorph, dimoxystrobin, diniconazole, dinocap, dithianon, dodecyl dimethyl ammonium chloride, dodemorph, dodine, doguadine, edifenphos, epoxiconazole, ethaboxam, ethirimol, ethyl (Z)-N-benzyl-N([methyl(methyl-thioethylideneaminooxycarbonyl)amino]thio)-β-alaninate, etridiazole, famoxadone, fenamidone, fenarimol, fenbuconazole, fenfuram, fenhexamid, fenoxanil (AC 382042), fenpiclonil, fenpropidin, fenpropimorph, fentin acetate, fentin hydroxide, ferbam, ferinzone, fluazinam, fludioxonil, flumetover, flumorph, fluoroirnide, fluoxastrobin, fluquinconazole, flusilazole, flusulfamide, flutolanil, flutriafol, folpet, fosetyl-aluminium, fuberidazole, furalaxyl, furametpyr, guazatine, hexaconazole, hydroxyisoxazole, hymexazole, imazalil, imibenconazole, iminoctadine, iminoctadine triacetate, ipconazole, iprobenfos, iprodione, iprovalicarb, isopropanyl butyl carbamate, isoprothiolane, kasugamycin, kresoxim-methyl, LY186054, LY211795, LY 248908, mancozeb, maneb, mefenoxam, mepanipyrim, mepronil, metalaxyl, metalaxyl M, metconazole, metiram, metiram-zinc, metominostrobin, metra-fenone, MON65500 (N-allyl-4,5-dimethyl-2-trimethylsilylthiophene-3-carboxamide), myclobutanil, NTN0301, neoasozin, nickel dimethyldithiocarbamate, nitrothale-isopropyl, nuarimol, ofurace, organomercury compounds, orysastrobin, oxadixyl, oxasulfuron, oxolinic acid, oxpoconazole, oxycarboxin, pefurazoate, penconazole, pencycuron, phenazin oxide, phosphorus acids, phthalide, picoxystrobin, polyoxin D, polyram, probenazole, prochloraz, procymidone, propamocarb, propamocarb hydrochloride, propiconazole, propineb, propionic acid, proquinazid, prothioconazole, pyraclostrobin, pyrazophos, pyrifenox, pyrimethanil, pyroquilon, pyroxyfur, pyrrolnitrin, quaternary ammonium compounds, quinomethionate, quinoxyfen, quintozene, silthiofam (MON 65500), S-imazalil, simeconazole, sipconazole, sodium pentachlorophenate, spiroxamine, streptomycin, sulphur, tebuconazole, tecloftalam, tecnazene, tetraconazole, thiabendazole, thifluzamide, 2-(thiocyanomethylthio)-benzothiazole, thiophanate-methyl, thiram, tiadinil, timibenconazole, tolclofos-methyl, tolymuanid, triadimefon, triadimenol, triazbutil, triazoxide, tricyclazole, tridemorph, trifloxystrobin, triflumizole, triforine, triticonazole, validamycin A, vapam, vinclozolin, XRD-563, zineb, ziram, zoxamide and compounds of the formulae:

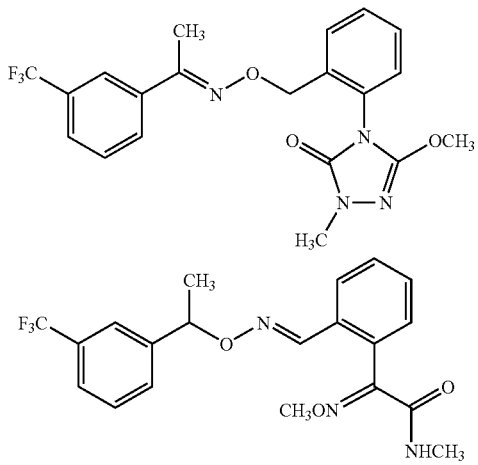

The compound of formula (I) may be mixed with soil, peat or other rooting media for the protection of plants against seed-borne, soil-borne or foliar fungal diseases.

Some mixtures may comprise active ingredients that have significantly different physical, chemical or biological properties such that they do not easily lend themselves to the same conventional formulation type. In these circumstances other formulation types may be prepared. For example, where one active ingredient is a water insoluble solid and the other a water insoluble liquid, it may nevertheless be possible to disperse each active ingredient in the same continuous aqueous phase by dispersing the solid active ingredient as a suspension (using a preparation analogous to that of an SC) but dispersing the liquid active ingredient as an emulsion (using a preparation analogous to that of an EW). The resultant composition is a suspoemulsion (SE) formulation.

The compound of the invention may be formulated for administration in any convenient way for use in veterinary or human medicine and the invention therefore includes within its scope pharmaceutical compositions comprising a compound of formula (I) adapted for use in veterinary or human medicine. Such compositions may be presented for use in conventional manner with the aid of one or more suitable pharmaceutically or veterinary acceptable carriers or excipients.

The compositions of the invention include those in a form formulated for parenteral, oral, rectal, topical or implant use.

For use in agriculture, horticulture or veterinary medicine it may be desirable to use the whole fermentation broth as a source of the active compound of the invention without separation into the individual compounds of formula (I). It may be suitable to use dried broth containing mycelia or to use lysed mycelia, live or dead mycelia separated from the broth using solid/liquid separation or evaporation techniques or to use the fermentation broth remaining after separation of the mycelia. If desired the broth or mycelia may be formulated into compositions including conventional inert carriers, excipients or diluents.

It will be understood by a person skilled in the art that in general the compounds of the invention may be used to combat infections by applying to the organism responsible for the infection or a location thereof an effective amount of a compound of formula (I).

In a further aspect the invention provides a process for the production of a compound of formula (I) which comprises the step of cultivating an organism of the strain *Streptomyces malaysiensis* capable of producing a compound of formula (I) whereby said compound is produced, and if desired isolating said compound therefrom.

Taxonomic studies have shown that a particular microorganism capable of producing compounds of formula (I) is a new strain of the microorganism *Streptomyces malaysiensis* hereinafter referred to as *Streptoinyces malaysiensis* JHCC 553434. A sample of this microorganism, which is a soil isolate, was deposited on 17 Dec. 2001 at the Deutsche Sammlung von Mikroorganismen und Zellkulturen GmbH (DSMZ), Mascheroder Weg 1b, D-38124 Braunschweig, Germany and has been assigned the Accession Number DSM 14702. The strain has been deposited under the terms and conditions of the Budapest Treaty and has been placed under restricted access under the terms of Rule 28(4) of the European Patent Convention. This new strain of *Streptomyces malaysiensis*, *Streptomyces malaysiensis* JHCC 553434 (DSM 14702) provides a further feature of this invention.

The invention also extends to further new strains of *Streptomyces malaysiensis* which possess the same essential morphological and cultural characteristics as *Streptomyces malaysiensis* JHCC 553434 (DSM 14702) and which are capable of producing a compound of formula (I).

The essential morphological and cultural characteristics assigned to *Streptomyces malaysiensis* JHCC 553434 (DSM 14702) are listed below:

Diagnostic aminoacid of peptidoglycan is: LL-diaminopimeli(ni)c acid

Mycolic acids are absent

Iso- and ante-iso fatty acids found, but no 10-methyl branched fatty acids

Base-sequence of 16s rDNA: similarity to other sequences of *Streptomyces species* >95%

Colour of colony: grey to dark-brown aerial mycelium and beige dirty-yellow substrate mycelium Formation of melanin or other diagnostic pigments not found Starch is hydrolysed Morphology: spores in short and narrow coils Physiology: according to Kaempfer et al. (J. Gen Microbiol. 13 1831–1891 (1991)):

utilisation of carbon sources =>100% cluster 18 : *S. violaceusniger*

Fatty acid-pattern: enough similarity (0.675) to *S. violaceusniger*

16s rDNA sequencing: comparison of partial sequence to *Streptomyces* library gave a similarity of 100% to *Streptomyces malaysiensis*, a member of group *S. violaceusniger*

Riboprint-pattern: enough similarity to group *S. violaceusniger*: Species *S. hygroscopicus* 0.83 and *S. malyasiensis* 0.82.

The species *Streptomyces malaysiensis* was recently described in literature: International Journal of Systematic Bacteriology (1999), 49, 1395–1402 by Amira Al-Tai et al.

The invention extends also to mutant strains of *Streptomyces malaysiensis* JHCC 553434 (DSM 14702) capable of producing a compound of formula (I). Mutants may be naturally occurring or may be produced by mutagenesis of the parent strain using conventional mutagenesis techniques such as genetic techniques such as recombination, transformation and selective techniques for spontaneous mutants; ionising radiation; chemical methods; heat.

The production of compounds of formula (I) by cultivation of a suitable strain of *Streptomyces malaysiensis* may be effected by conventional means i.e. by culturing the microorganism in the presence of assimilable sources of carbon, nitrogen and mineral salts.

The strain of *Streptomyces malaysiensis* according to the invention is preferably *Streptoinyces malaysiensis* JHCC 553434 (DSM 14702).

Assimilable sources of nitrogen, carbon, and minerals may be provided by either simple or complex nutrients. Sources of carbon will generally include amino acids; alkanes; molasses; glycerides; glycerol; glucose, maltose, lactose, sucrose, fructose, starch, dextrin, carboxylic acids, alcohols, and vegetable oils. Sources of carbon will generally comprise form 0.5% to 10% by weight of the fermentation medium.

Sources of nitrogen will generally include soya bean meal, corn steep liquors, yeast extracts, cottonseed meal, peptones, malt extract, molasses, casein, amino acid mixture, ammonia, ammonium salts or nitrates, urea and other amides. Sources of nitrogen will generally comprise from 0.1% to 10% by weight of the fermentation medium.

Nutrient mineral salts which may be incorporated into the culture medium include for example, salts capable of generating sodium, potassium, ammonium, iron, magnesium, zinc, nickel, cobalt, manganese, vanadium, chromium, calcium, copper, molybdenum, boron, phosphate, sulphate, chloride and carbonate ions.

Cultivation will desirably take place with aeration and agitation. The cultivation will generally be carried out in the pH range 5 to 8, preferably 6 to 7, most preferably pH 6.5. The microorganism of the invention will generally be cultivated at a temperature of from 20° to 50° C., preferably from 25° to 40° C. and most especially at 28° or 35° C. The fermentation may be carried out for a period of 2–14 days, e.g. 6 to 8 days.

Where it is desired to separate a compound of the invention from the whole fermentation broth this may be achieved using conventional isolation and separation techniques. The compounds of the invention are found predominantly in the fermentation broth but small amounts may be found in the mycelia of the cells.

In a further aspect the invention provides a compound of formula (I) in the form of a whole fermentation broth containing such a compound; the solids of a whole fermentation broth containing such a compound; intact or lysed mycelia separated from a whole fermentation broth containing such a compound; or the solids of such a whole fermentation broth containing such a compound after separation of intact or lysed mycelia; or such a whole fermentation broth containing such a compound after the separation of the mycelia and all solids.

In a yet further aspect the invention provides a composition comprising an effective amount of a compound of formula (I) which may be in a form according to the above aspect of the invention.

The compounds of the invention may be isolated and separated by a variety of fractionation techniques, for example, adsorption-elution, precipitation, fractional crystallisation and solvent extraction which may be combined in various ways.

Centrifugation and chromatography have been found to be most suitable for isolating and separating the compounds of the invention.

Following the fermentation, the mycelia may be harvested using conventional techniques such as filtration or centrifugation. The compounds of the invention are found mainly in the aqueous medium and may be separated from the mycelia, for example by centrifugation, followed by extraction of the mycelium with water or an appropriate water miscible solvent such as a lower ketone e.g. acetone; a lower alcohol e.g. methanol or ethanol; or a lower diol.

Generally more than one extraction is desirable to achieve optimum recovery. Preferably the first extraction is performed using water or a water-soluble solvent, preferably methanol. The compounds of the invention may then be recovered as crude extracts by removal of the solvent e.g. by evaporation. The concentrate may then be redissolved in an aqueous medium e.g. water, and further purified by further centrifugation of any residual solids. Removal of the water or water miscible solvent yields a compound of formula (I).

Purification of the compounds of the invention may be effected by conventional techniques such as for example chromatography, preferably high performance liquid chromatography, on a suitable support. The support may be in the form of a bed or preferably packed in a column.

A solution of the compounds in a suitable solvent will generally be loaded on to the silica, if desired after reducing the volume of the solvent. The column may optionally be washed and eluted with a solvent of suitable polarity. In the case of silica, alcohols such as methanol in combination with water may be used.

Elution and separation of the compounds of the invention may be monitored by conventional techniques such as chromatography preferably high performance liquid chromatography.

The compounds of the invention may be further purified by crystallisation and the invention extends also to a compound of formula (I) in crystalline form.

The invention further extends to a process for combating fungi or viruses or cancer cells comprising exposing said viruses or fungi or cancer cells to a compound of formula (I).

The invention extends also to the use of a compound of formula I with a biological system that has modified or enhanced resistance to fungi and/or viruses. The biological system may for example be a plant, or may be a mammalian system such as an organ, tissue or cell thereof. In the case of a plant system the enhanced resistance may have been introduced into the plant using conventional breeding techniques where plants showing enhanced resistance are selected over may generations. Alternatively or as well as, the enhanced resistance may due to the introduction into said plant by genetic modification recombinant DNA techniques of one or more DNA sequences, the expression of which enhances the resistance of the host plant. This approach is often referred to as integrated crop management.

In a further aspect therefore the invention provides a method of controlling fungal infection of a plant or part thereof said plant having been genetically modified to enhance resistance to fungi either by selective breeding and/or preferably by genetic modification where one or more DNA sequences, the expression of which enhances the resistance of the plant to fungi, have been introduced into said plant using recombinant DNA techniques, said method comprising exposing said plant or part thereof to a compound of formula (I).

In a further aspect therefore the invention provides a method of controlling viral infection of a plant or part thereof said plant having been genetically modified to enhance resistance to viruses either by selective breeding and/or preferably by genetic modification where one or more DNA sequences, the expression of which enhances the resistance of the plant to viruses, have been introduced into said plant using recombinant DNA techniques, said method comprising exposing said plant or part thereof to a compound of formula (I).

In a yet further aspect the invention provided the use of a compound of formula (I) as a biocidal agent.

In a preferred embodiment of this aspect the invention provides the use of a compound of formula (I) as an anti-fungal agent.

In a further embodiment of this aspect the invention provides the use of a compound of formula (I) as an anti-viral agent.

In a further embodiment of this aspect the invention provides the use of a compound of formula (I) as an anti-cancer agent.

The invention is illustrated by the following Examples:

EXAMPLE 1

Standard Procedure for Production of Compounds of Formula (I)

Shake flasks in M3 media pH controlled (MES)

Producer strain *Streptomyces malaysiensis*. JHCC-553434 was grown on agar slants and plates. It was transferred to TSM-40 and TSM-7/2 to grow up for strain preservation. Better growth was found in TSM-7/2 and it was used for routine strain preservation procedure. A stock of −80° C. cryovials was produced as start material for all following experiments. HPLC—MS trials using the supernatant of those cultures (4–6 days at 35° C.) show production of a compound of formula (I).

| TSM-40 for 1l | |
|---|---|
| Glucose (Merck) | 4 g |
| Malt Extract (Difco) | 10 g |
| Yeast Extract | 4 g |
| pH corrected before sterilisation to 7 | |
| TSM-7/2 for 1l | |
| Mannit | 20 g |
| Soytone | 10 g |
| Soyabean Oil | 2.5 g |
| $K_2HPO_4$ | 0.35 g |
| $CaCO_3$ | 0.5 g |
| pH corrected before sterilisation to 7 | |

Setup of Production in Shake Flasks

Inoculum: As starting material good grown 1×ISP-2 agar plates were used and incubated at 35° C. about 5 days.

Seed culture

VK1: 1×SC-02 medium (100 ml in 1 baffled EMK 500 ml) was inoculated with biomass from agar plates and incubated for 3 days at 35° C. and 120 rpm on a rotary shaker.

Main culture: 150×M3 medium (60 ml in 1 baffled EMK 500 ml) were inoculated with 5 vol % of SC-01 and incubated on the rotary shaker at 35° C. and 120 rpm. Media were buffered using 100 mM MES buffer (Good's buffer) and pH was adjusted to 6.5 (NaOH) prior to autoclaving. (MES Buffer is 2-N-morpholino ethanesulfonic acid hydrate, minimum 99.5 % titration, $C_6H_{13}NO_4S$ 1M=195.2 g, pKa=6.1 at 25° C., pH range 5.5–6.7. Producer SIGMA ,ART. Nr. M8250)

Samples and Analysis: Samples were checked on days 4, 5 and 6. Growth was recorded and 1 ml samples were centrifuged (Biofuge A- Heraeus Sepatec, 10 min 10 000 rpm, RT). The supernatant was separated and biomass was discarded. All the supernatants were filtered. Clear supernatants were transferred to HPLC vials and measured in a Waters LC/MS system (HPLC: Alliance 2790 with photodiode array detector, MS: micromass ZQ).

Harvest and Analysis: After 6 days all flasks were harvested and centrifuged. Supernatant and Biomass were stored at −20 C.

MEDIA:

| SC-02 For 1l medium: | |
|---|---|
| Glucose (Merck) | 10 g |
| Starch soluble (Merck) | 10 g |
| Peptone (Sigma) | 10 g |
| Yeast extract (Difco) | 2 g |
| $MgSO_4 \times 7H_2O$ (Merck) | 1 g |
| pH 6.5 | |
| M3 For 1l medium: | |
| Glucose | 20 g |
| Starch sol. | 10 g |
| Soyaflower | 25 g |
| Yeast Extract | 4 g |
| Meat Extract | 1 g |
| Component A | 10 ml |
| Component A: For 1l add before sterilisation: | |
| NaCl | 0.5 g |

-continued

| | |
|---|---|
| CaCO$_3$ | 0.5 g |
| MgSO$_4$ × 7H$_2$O | 0.5 g |
| KH$_2$PO$_4$ | 50 mg |
| FeCl$_3$ × 6H$_2$O | 16.7 mg |
| ZnSO$_4$ × 7H$_2$O | 21.2 mg |
| CaCl$_2$ × 2H$_2$O | 6.5 mg |
| CuSO$_4$ × 5H$_2$O | 5 mg |
| MnCl$_2$ × 4H2O | 5 mg |

In general 1 l of 100× concentrated stock solution is prepared. From stock solution 10 ml/l is used. Stock solution has to be stored at 4° C.

EXAMPLE 2

Isolation and physical/chemical characterisation of Compounds of Formula (I)

Lyophilisate (23 g), which corresponds to 1 l of fermentation broth of *Streptomyces malaysiensis* JHCC-553434 prepared as described in Example 1, were dissolved in water and transferred to a G-25 column (Sephadex, 70 mm×780 mm, 1 ml/min). After elution with water, the fraction containing the compounds of formula (I) was lyophilised. The residue, 0.678 g, was purified on a medium-pressure chromatography on silica gel (Silica 32-63, 60 Angström, 55 mm×500 mm, 22 ml/min) with a gradient of acetonitrile: water and yielded after evaporation, 0.143 g of enriched material. Further separation by means of high-pressure chromatography on RP silica gel (Kromasil 100, C18, 10 μm, 20 mm×250 mm, 10 ml/min), with a gradient of acetonitrile: water, yielded a first fraction of 0.058 g of the compound of formula (I) where R is H and a second fraction of 0.034 g of the pure compound of formula (I) where R is CH$_3$. 0.014g Of the first fraction were further purified on reverse phase silica gel (Develosil RPAQUEOUS, 5 μm, 20×250 mm, flow rate 10 ml/min, detection wavelength 220 nm, 4 runs) with pure water as eluant. The peak that eluted after 30 minutes contained the compound of formula (I) where R is H. Lyophilisation of the fraction yielded 0.004 g of the pure compound of formula (I) where R is H.

EXAMPLE 3

Characterising Structural Data for the Compound of Formula (I) where R is CH$_3$

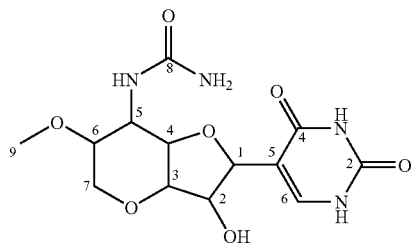

NMR Data $^1$H spectrum, run 2% w/v solution in D$_2$O, referenced to residual HOD peak at δ 4.63. Data in { } was run as 0.5% w/v solution in D6-DMSO, referenced to HD5-DMSO at δ 2.49. Spectra were run on a JEOL GX400 Spectrometer operating at 399.6 MHz

| δ | Carbon to which H's bonded | Multiplicity and Number of H's | Coupling constant in Hz |
|---|---|---|---|
| 3.26 | C9 | s (3H) | |
| 3.37 | C7 | t (1H) | 11.4 |
| 3.48 | C3 | dd (1H) | 10.8, 4.8 |
| 3.67 | C6 | ddd (1H) | 11.5, 5.6, 4.3 |
| 3.83 | C4 | dd (1H) | 10.8, 3.8 |
| 3.92 | C7 | dd (1H) | 11.4, 5.6 |
| 4.14 | C2 | d {d}(1H) | 4.8, {4.0} |
| 4.71 | C1 | dd (1H) | 1.3, 0.7 |
| 4.80 | C5 | m (1H) | |
| {5.12} | C2 | d (1H) OH | 4.0 |
| {6.30} | C8 | d (1H) NH | 10.5 |
| 7.41 | Uracil C6 | d (1H) | 1.3 |
| {10.85} | | Uracil NH's and urea NH$_2$ | | s = singlet
d = doublet
dd = double doublet
ddd = double double doublet
t = triplet
m = multiplet $^{13}$C spectrum, run 2% w/v solution in D$_2$O, referenced to D6-acetone {(CD$_3$)$_2$CO} at δ29.8, using JEOL GX400 NMR spectrometer operating at 100.4 MHz

| δ | Carbon | Multiplicity |
|---|---|---|
| 47.3 | C5 | d (broadened) |
| 56.2 | C9 | q |
| 65.2 | C7 | t |
| 70.8 | C2 | d |
| 73.2 | C3 | d |
| 73.3 | C6 | d |
| 74.4 | C4 | d |
| 83.4 | C1 | q |
| 111.4 | Uracil C5 | s |
| 139.0 | Uracil C6 | d |
| 152.6 | Uracil C2 | s |
| 161.2 | C8 | s |
| 164.5 | Uracil C4 | s | s = singlet
d = doublet
t = triplet
q = quartet

The terms above relate to signals off-resonance multiplicity as determined by DEPT (135) spectrum.

On the basis of the above nmr data it is believed that the stereochemistry is as shown below.

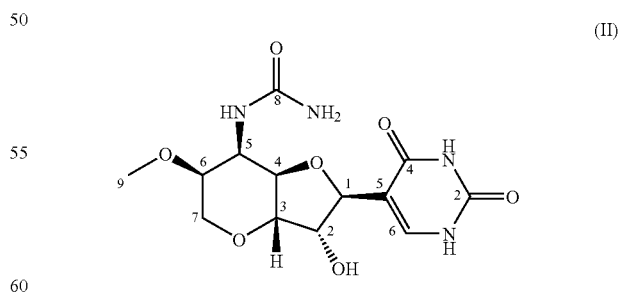

(II)

This compound (II) is here named Malayamycin A.

Mass Spectrometry

Ionisation by fast atom bombardment in glycerol and water gives an m/z of 343 [M+H]+ and m/z of 365 [M+Na]+, consistent with a molecular weight of 342.

Accurate mass measurement gave a molecular weight as 342.1197 mass units consistent with the molecular formula of $C_{13}H_{18}N_4O_7$.

Characterising Structural Data for Compound of Formula (I) where R is H

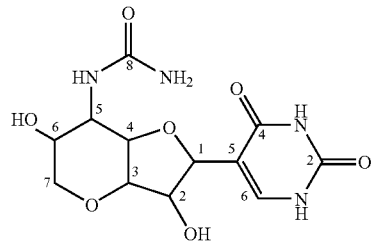

NMR Data $^1$H NMR spectrum, run 2% w/v solution in $D_2O$, referenced to residual HOD peak at δ 4.63. Data in { } was run as 2% w/v solution in D6-DMSO, referenced to HD5-DMSO at δ 2.49. Spectra were run on a Varian Unity INOVA 500 NMR Spectrometer operating at 499.9 MHz and 25° C.

| δ | Assignment | Multiplicity and Number of H's | Coupling constants in Hz |
|---|---|---|---|
| 3.36 | H-7 | t (1H) | 11.5 |
| 3.46 | H-3 | dd (1H) | 10.8, 4.8 |
| 3.79 | H-7 | dd (1H) | 11.5, 5.6 |
| 3.83 | H-4 | dd (1H) | 10.8, 3.6 |
| 3.95 | H-6 | ddd {d} (1H) | 11.5, 5.6, {5.0}, 4.0 |
| 4.13 | H-2 | d {d} (1H) | 4.8, {4.1} |
| 4.55 | H-5 | tb (1H) | |
| 4.69 | H-1 | s (1H) | |
| {5.06} | C6 OH | {d} (1H) | {5.0} |
| {5.25} | C2 OH | {d} (1H) | {4.1} |
| {5.46} | C8 NH2 | {s} (2H) | |
| {6.14} | C8 NH | {db} (1H) | {10} |
| 7.22 | Uracil C6 | s (1H) | |
| {10.96}, {11.10} | Uracil NH's | {sb} (1H each) | |

The coupling constants are almost identical to those of compound (I) where R is CH$_3$.
This shows that the configurations of the compound (I) where R is CH$_3$ and the compound (I) where R is H are also identical.
s = singlet
d = doublet
dd = double doublet
ddd = double double doublet
t = triplet
b = broad $^{13}$C NMR spectrum, run 2% w/v solution in $D_2O$, referenced to dioxane at δ 67.4 ppm, using a Varian Unity INOVA 500 NMR spectrometer operating at 125.7 MHz and 25° C.

| δ | Carbon | Correlates with |
|---|---|---|
| 51.8 (signal broad) | C5 | H-5 |
| 65.5 | C6 | H-6 |
| 67.9 | C7 | H-7 |
| 71.9 | C2 | H-2 |
| 74.1 | C3 | H-3 |
| 75.5 | C4 | H-4 |
| 84.6 | C1 | H-1, Uracil H-6 |
| 112.5 | Uracil C5 | H-1, H-2, Uracil H-6 |
| 140.1 | Uracil C6 | H-1, Uracil H-6 |
| 153.7 | Uracil C2 | Uracil H-6 |
| 162.7 | C8 | |
| 165.6 | Uracil C4 | H-1, Uracil H-6 |

The correlations were as observed in the HSQC and HMBC spectra.

On the basis of the above nmr data it is believed that the stereochemistry is as shown below.

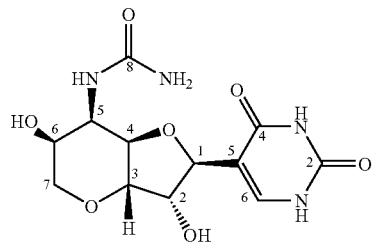

This compound (III) is here named Desmethylmalayamycin A.

Mass Spectrometry

Ionisation by electrospray ionisation gives an m/z of 329 [M+H]+ and m/z of 351 [M+Na]+, consistent with a molecular weight of 328.

Accurate mass measurement gave a molecular weight as 329.1101 mass units consistent with the molecular formula of $C_{12}H_{16}N_4O_7$.

EXAMPLE 4

This Example illustrates the fungicidal properties of the compounds of formula (I). The compounds were tested against a variety of foliar fungal diseases of plants. The technique employed was as follows.

Plants were grown on an artificial, cellulose based growing medium. The test compounds were individually diluted in reverse osmosis water to a final concentration of 100 ppm in water (that is, 1 mg of compound in a final volume of 10 ml) immediately before use. TWEEN 20 (at a final concentration of 0.05% by volume) was added with the water to improve retention of the spray deposit. TWEEN is a registered trade mark.

The compounds were applied to the foliage of the test plants by spraying the plant to maximum droplet retention.

These tests were carried out against *Stagonospora Nodorum* (LEPTNO), *Blumeria graminis* f.sp. *tritici* (ERYSGT), and *Puccinia triticina* (PUCCRT) on wheat. Two replicates, each containing 3 plants were used for each treatment. The plants were inoculated with either a calibrated fungal spore suspension or a "dusting" with dry spores 6 hours or one day after chemical application.

After chemical application and inoculation, the plants were incubated under high humidity conditions (except those inoculated with *Blumeria graminis* f.sp. *tritici*) and then put into an appropriate environment to allow infection to proceed until the disease was ready for assessment. The time period between chemical application and assessment varied from six to nine days according to the disease and environment. However, each individual disease was assessed after the same time period for all compounds.

Assessments were carried out collectively on the plants in each replicate and averaged to give one result per replicate.

The disease level present (the percentage leaf area covered by actively sporulating disease) was assessed visually. For each treatment, the assessed values for all its replicates were meaned to provide mean disease values. Untreated control plants were assessed in the same manner. The data were then processed (see formula below) to calculate a PRCO (Percentage Disease Reduction from Control) value.

Banded Assesment Method and Calculation of PRCO Values

The mean disease values are banded in the manner shown below. If the disease level value falls exactly mid-way between two of the points, the result will be the lower of the two points.

| | |
|---|---|
| 0 = | 0% disease present |
| 1 = | 0.1–1% disease present |
| 3 = | 1.1–3% disease present |
| 5 = | 3.1–5% disease present |
| 10 = | 5.1–10% disease present |
| 20 = | 10.1–20% disease present |
| 30 = | 20.1–30% disease present |
| 60 = | 30.1–60% disease present |
| 90 = | 60.1–100% disease present |

An example of a typical banded calculation is as follows:
Mean disease level for treatment A=25%
Therefore banded mean disease level for treatment A=30
Mean disease level on untreated controls=85%
Therefore banded mean disease level on untreated controls=90

$$PRCO = 100 - \frac{\{\text{Banded mean disease level for treatment } A\}}{\{\text{Banded mean disease level on untreated controls}\}} \times 100$$

$$= 100 - \frac{(30 \times 100)}{90} = 66.7$$

The PRCO is then rounded to the nearest whole number; therefore, in this particular example, the PRCO result is 67. It is possible for negative PRCO values to be obtained. PRCO results are shown below.

TABLE I

| COMPOUND NO. | ERYSGT 6 hour Protectant | PUCCRT 1 day Protectant | LEPTNO 1 day Protectant |
|---|---|---|---|
| (II) | 100 | 100 | 100 |
| (III) | 0 | 100 | 99 |

Key to Table I
ERYSGT = *Blumeria graminis tritici*
PUCCRT = *Puccinia triticina*
LEPTNO = *Stagonospora Nodorum*

What is claimed is:

1. A compound having the formula (I)

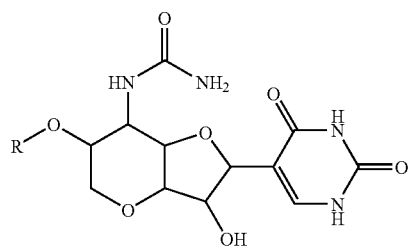

(I)

wherein R is H or CH$_3$.

2. A compound according to claim 1 having the formula (II)

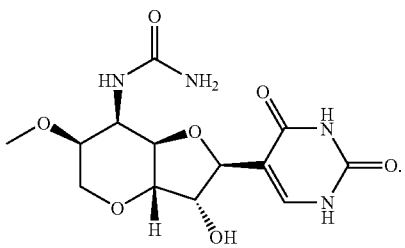

(II)

3. A compound according to claim 1 having the formula (III)

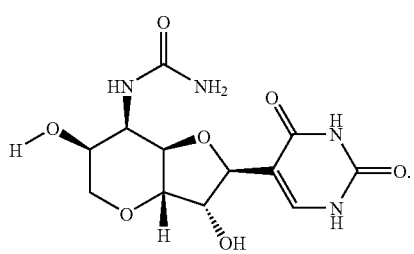

(III)

4. A compound according to claim 1 in the form of a whole fermentation broth containing such a compound; the solids of a whole fermentation broth containing such a compound; intact or lysed mycelia separated from a whole fermentation broth containing such a compound; the solids of such a whole fermentation broth containing such a compound after separation of intact or lysed mycelia; or such a whole fermentation broth containing such a compound after the separation of solids and the mycelia.

5. A biocidal composition comprising a biocidally effective amount of a compound of formula (I) according to claim 1.

6. A composition according to claim 5 wherein said composition is a fungicidal composition comprising a fungicidally effective amount of a compound of formula (I) and a suitable carrier or diluent therefor.

7. A method of combating and controlling fungi which comprises treating the fungi or the locus of the fungi with a composition according to claim 6.

8. A method of combating or controlling phytopathogenic fungi according to claim 7 which comprises applying a fungicidally effective amount of a compound of formula (I), or a composition containing a compound of formula (I), to a plant, to a seed of a plant, to the locus of the plant or seed or to soil or any other plant growth medium.

9. The method of claim 8 wherein the plant growth medium comprises a nutrient solution.

* * * * *